US005855617A

United States Patent [19]
Orton

[11] Patent Number: 5,855,617
[45] Date of Patent: Jan. 5, 1999

[54] TREATED TISSUE FOR IMPLANTATION AND METHODS OF TREATMENT AND USE

[75] Inventor: E. Christopher Orton, Fort Collins, Colo.

[73] Assignee: Colorado State University Research Foundation, Fort Collins, Colo.

[21] Appl. No.: 712,726

[22] Filed: Sep. 12, 1996

Related U.S. Application Data

[63] Continuation of Ser. No. 23,492, Feb. 26, 1993, Pat. No. 5,772,695, which is a continuation of Ser. No. 664,902, Mar. 5, 1991, Pat. No. 5,192,312.

[51] Int. Cl.$^6$ ........................................................ A61F 2/62
[52] U.S. Cl. ................................................................ 623/11
[58] Field of Search ............................... 623/1, 2, 11, 12, 623/66; 128/898; 435/1.2, 378, 402, 395; 424/422, 423, 424, 425

[56] References Cited

U.S. PATENT DOCUMENTS

| | | |
|---|---|---|
| 3,966,401 | 6/1976 | Hancock et al. . |
| 4,240,794 | 12/1980 | Holman et al. . |
| 4,323,358 | 4/1982 | Lentz et al. . |
| 4,378,224 | 3/1983 | Nimni et al. . |
| 4,383,832 | 5/1983 | Fraefel et al. . |
| 4,402,697 | 9/1983 | Pollock et al. . |
| 4,405,327 | 9/1983 | Pollock . |
| 4,407,787 | 10/1983 | Stemberger . |
| 4,485,096 | 11/1984 | Bell . |
| 4,539,716 | 9/1985 | Bell . |
| 4,546,500 | 10/1985 | Bell . |
| 4,553,974 | 11/1985 | Dewanjee . |
| 4,559,298 | 12/1985 | Fahy . |
| 4,567,847 | 2/1986 | Linner . |
| 4,609,551 | 9/1986 | Caplan . |
| 4,642,120 | 2/1987 | Nevo et al. . |
| 4,647,283 | 3/1987 | Carpentier et al. . |

(List continued on next page.)

FOREIGN PATENT DOCUMENTS

| | | |
|---|---|---|
| 0267026 | 11/1987 | European Pat. Off. . |
| 0296475 | 12/1988 | European Pat. Off. . |
| 0361957 | 4/1990 | European Pat. Off. . |
| 0 475 409 A2 | 3/1992 | European Pat. Off. . |
| 0 564 786 A2 | 10/1993 | European Pat. Off. . |
| 1522286 | 2/1967 | France . |
| 2104349 | 8/1971 | France . |
| 2589165 | 4/1987 | France . |
| 2136533 | 9/1984 | United Kingdom . |
| WO 83/03335 | 10/1983 | WIPO . |
| WO 84/01879 | 5/1984 | WIPO . |
| WO 86/02273 | 4/1986 | WIPO . |
| WO 88/02263 | 4/1988 | WIPO . |
| WO 89/00198 | 1/1989 | WIPO . |
| WO 89/01286 | 2/1989 | WIPO . |
| WO 89/08117 | 9/1989 | WIPO . |
| WO 91/16009 | 10/1991 | WIPO . |
| WO 91/18505 | 12/1991 | WIPO . |

OTHER PUBLICATIONS

"Porcine Heterograft Valve Replacement in Children", by D.B. Williams, MD, G.K. Danielson, MD, D.C. McGoon, MD, F.J. Puga, MD, D.D. Mair, MD and W.D. Edwards MD, *J. Thorac Cardiovasc Surg* 84: pp. 446–450, Sep. 1982.

"Mechanical Testing of Cryopreserved Aortic Allografts Comparison with Xenografts and Fresh Tissue", by I. Vesely, PhD, L.Gonzalez–Lavin, MD, D. Graf and D. Goughner, MD, PhD, FRCPC, *Journal of Thoracic and Cardiovascular Surgery, St. Louis*, vol. 99, No. 1, pp. 119–123, Jan. 1990.

(List continued on next page.)

*Primary Examiner*—David J. Isabella
*Attorney, Agent, or Firm*—Kenyon & Kenyon

[57] ABSTRACT

Tissue which is suitable for transplant is treated with a growth factor and cells which populate the tissue and native cells must be removed, they cannot be "masked" reduce immunogenicity; this increases the longevity of the tissue upon transplant. The preferred growth factor is basic fibroblast growth factor, and the preferred cells are fibroblasts. The tissue can be an allograft or xenograft taken from a cow, pig or other mammal.

16 Claims, 2 Drawing Sheets

U.S. PATENT DOCUMENTS

| | | |
|---|---|---|
| 4,648,881 | 3/1987 | Carpentier et al. . |
| 4,688,387 | 8/1987 | Conaway . |
| 4,707,998 | 11/1987 | Linner et al. . |
| 4,776,853 | 10/1988 | Klement et al. . |
| 4,785,079 | 11/1988 | Gospodarowicz . |
| 4,798,611 | 1/1989 | Freeman, Jr. . |
| 4,799,361 | 1/1989 | Linner . |
| 4,801,299 | 1/1989 | Brendel et al. . |
| 4,828,563 | 5/1989 | Muller-Lierheim . |
| 4,835,102 | 5/1989 | Bell et al. . |
| 4,838,888 | 6/1989 | Nashef . |
| 4,870,160 | 9/1989 | Charonis et al. . |
| 4,878,913 | 11/1989 | Aebischer et al. . |
| 4,890,457 | 1/1990 | McNally et al. . |
| 4,902,782 | 2/1990 | Gospodarowicz . |
| 4,911,710 | 3/1990 | Milthorpe et al. . |
| 4,950,483 | 8/1990 | Ksander et al. . |
| 4,960,424 | 10/1990 | Grooters . |
| 4,964,280 | 10/1990 | Piunno et al. . |
| 4,973,493 | 11/1990 | Guire . |
| 5,000,963 | 3/1991 | Hefton . |
| 5,002,566 | 3/1991 | Carpentier et al. . |
| 5,032,508 | 7/1991 | Naughton et al. ........................ 435/32 |
| 5,131,850 | 7/1992 | Brockbank . |
| 5,145,770 | 9/1992 | Tubo et al. . |
| 5,192,312 | 3/1993 | Orton . |
| 5,197,985 | 3/1993 | Caplan et al. . |
| 5,215,541 | 6/1993 | Nashef et al. . |
| 5,219,576 | 6/1993 | Chu et al. . |
| 5,336,616 | 8/1994 | Livesey et al. . |
| 5,474,770 | 12/1995 | Broly et al. . |

OTHER PUBLICATIONS

"An Approach to the Optimization of Preparation of Bio-prosthetic Heart Valves", by D. Mavrilas and Yannis Missirlis, *J. Biomechanics*, vol. 24, No. 5 pp. 331–339, 1991.

Residual Heteroantigencity of Glutaraldehyde–Treated Porcine Cardiac Valves, by M.L. Villa, S. DeBiasi and F. Pilotto, *Tissue Antigens*, vol. 16, pp. 62–29, 1980.

"Tissue–Derived Biomaterials and Their Use In Cardiovascular Prosthetic Devices", by S.L. Hilbert, V.J. Ferrans, and M. Jones, *Medical Progress Through Technology* , vol. 14, pp. 115–153, 1988.

"Characterization of Pepsin–Solubilized Bovine Heart–Valve Collagen", by R.I. Bashey, H.M. Bashey and S.A. Jimenez, *Biochem Journal*, vol. 173, pp. 885–894, 1978.

"Collagen Heterogeneity in Pig Heart Valves", by P. Mannschott, D. Herbage, M. Weiss and C. Buffevant, *Biochimica et Biophysica Acts* , vol. 434, pp. 177–183, 1976.

"Preservation of Aortic Heart Valves with Maintenance of Cell Viability", by A.W. M. Van Der Kamp, MD, W.J. Visser, J.M. Van dongen, Ph.D., J. Nauta, MD and H. Galjaard, MD, *Journal of Surgical Research* , vol. 30, pp. 47–56, 1981.

"Viability of Connective Tissue Cells Following Storage of Aortic Valve Leaflets", by D.D. Reichenbach, MD, H. Mohri, MD, M. Sands and K.A., Merendino, MD, *Journal of Thoracic and Cardiovascular Surgery*, vol. 62, No. 5, pp. 690–695, Nov. 1971.

"Aortic Valve Replacement with Frozen Irradiated Homografts", by P.M. Beach, Jr., MD, F.O. Bowman, Jr., MD, G.A. Kaiser, MD, E. Parodi, MD and J.R. Malm, MD, *Department of Surgery, College of Physcians and Surgeons, Columbia University, Supplement I to Circulation*, vols.XLV and XLVI, pp. I–29—I 35, May 1972.

"Histological Assessment of Orthotopic Aortic Valve Leaflet Allografts: Its Role in Selecting Graft Pre–Treatment" by L.C. Armiger, J.B. Gavin and B.G. Barratt–Boyes, *Pathology*, vol. 15, pp. 67–73, 1983.

"A Comparison of Aortic Valve Replacement with Viable Cryopreserved and Fresh Allograft Valves, With a Note on Chromosomal Studies", by M.F. O'Brien, FRACS, FRCS, E. G. Stafford,FRACS, FACS, M.A.H. Gardner, FRACS, P.G. Pohlner, FRACS, D.C. McGiffin, FRACS, J.W. Kirklin, MD, *Journal of Thoracic and Cardiovasular Surgery*, vol. 94, No. 6, pp. 812–823, Dec. 1987.

"Cryopreserved Viable Allograft Aortic Valves", by M.F. O'Brien, E.G. Stafford, M.A.H. Gardner, P. Pohlner, D.C. McGrinnin, M. Johnston, P. Tesar, A. Brosnan, P. Duffy, *(Prince Charles Hospital)*, Brisbane, Australia, pp. 311–321.

"The Viable Cryopreserved Allograft Aortic Valve", by M.F. O'Brien, FRACS, G. Stafford, FRACS, M. Gardner, FRACS, P. Pohlner, FRACS, D. McGiffin, FRACS, N. Johnston, FRACPA, A. Brosnan, B.Sc, and P. Duffy, MBBS, PhD, *J. Cardiac Surg*, vol. 1, No. 3, Supplement, pp. 153–167, 1987.

"Durability of The Viable Aortic Allograft", by W.W. Angell, MD, J.H. Oury, MD, J.J. Lamberti, MD and J. Koziol, PhD, *J. Cardiovaic Surg*, vol. 98, pp. 48–56, 1989.

"Xenotransplantation: A View to the Future", by F.H. Bach, *Transplantation Proceedings*, vol. 25, No. 1, pp. 25–29, Feb. 1993.

"New Biologic and Synthetic Vascular Prostheses", by H.P. Greisler, MD, *Medical Intelligence Unit*, Chapter 3, Biohybrids–Biological Coatings In Synthetic Grafts, pp. 33–46.

"Immunological Aspects of Treated Natural Tissue Prostheses", by P.K. Bajpai, Chapter 2, vol. 1, pp. 5–25.

"Improved Endothelial Viability of Heart Valves Cryopreserved by a New Technique", by E.J. Feng, C.E. van Hove, R. Mohan, L. Andries, M. Rampart, A.G. Herman and P.J. Walter, *Eur J. Cardio–Thoracic Surgery*vol. 6, pp. 251–155, 1992.

"Xenografts—Future Prospects for Clinical Transplantation", by T.D.H. Cairns, D.H. Taube, N. Stevens, R. Binns and K.I. Welsh, *Immunology Letters*, vol. 29, pp. 167–170, 1991.

"Transplantation Immunology", by C.H. Kirkpatrick, MD, D.T. Rowlands, Jr., MD, *JAMA*, vol. 268, No. 20, pp. 2952–2958, Nov. 25, 1992.

"Cryopreservation Does Not Alter Antigenic Expression of Aortic Allografts", by R.P. Cochran, MD and K.S. Kunzelman, BS,*Journal of Surgical Research*, vol. 46, pp. 597–599, 1989.

"Effect of Cryopreservation on the Presence of Endothelial Cells on Human Valve Allografts", by F.M. Lupinetti, MD, T.T. Tsai, J.M. Kneebone, MS and E.L. Bove, MD,*J. Thorac Cardio–Vasc Surg*, vol. 106, pp 912–917, 1993.

"Effects of Cell Removal Upon Heart Valve Leaflet Mechanics and Immune Responses in a Xenogeneic Model", by S. Goldstein & K. Brockbank, *Poster Abstracts*, P29.

"Lack of Cross–Species Sensitization Between Skin Allo–and Xenotransplants in Mice", by C. Vizler, T. Janossy, Z. Tabi, P. Vegh, Institute of Experimental Surgery, *Poster Abstracts*, P30.

"Failure of Cryopreserved Homograft Valved Conduits in the Pulmonary Circulation", by D.C. Cleveland, MD, W.G. Williams, MD, A.J. Razzouk, MD, G.A. Trusler, MD, I.M. Rebeyka, MD, L. Duffy, PhD, Z. Kan, MD, J.G. Coles, MD and R.M. Freedom, MD, (circulation from the Divisions of Cardiovascular Surgery and Cardiology, The Hospital for Sick Children, II pp. 150–153).

"Degeneration of Aortic Valve Allografts in Young Recipients", by D. R. Clarke, MD, D.N. Campbell, MD, A.R. Hayward, MD, PhD and D.A. Bishop, BS, *J Thorac Cardiovasc Surg*, vol. 105, pp. 934–942, 1993.

"Immunogenicity of Tanned Tissue Valve Xenografts" by P.K. Bajpai, *Biomaterials in Cardiovascular Surgery, General Surgery and Neurosurgery*, Chapter 47, pp. 735–752.

"Xenotransplantation: A Current Perspective", by F.H. Bach, A.P. Dalmasso and J.L. Platt, *Transplantation Reviews*, vol. 6, No. 3, pp. 163–174, Jul. 1992.

"Endothelial Cell Replication in an In Vivo Model of Aortic Allografts", by F.M. Lupinetti, MD, T.T. Tsai, and J.M. Kneebone,MS, *Ann Thorac Surg*, vol. 56, pp. 237–241, 1993.

"Endothelial Cell Growth Factor Attachment to Biomaterials", by H.P. Greisler, J.Klosak, J.W. Dennis, J. Ellinger, D.U. Kim, W. Burgess and T. Maciag,*Trans Am Soc. Artif Intern Organs*, vol. XXXII, pp. 346–349, 1986.

Biomaterial pretreatment with ECGF to Augment Endothelial Cell Proliferation, by H.P. Greisler, MD, J.J. Klosak, M.D., J.W. Dennis,MD, S.M. Karesh, PhD, J. Ellinger and D.U. Kim, MD, *Journal of Vascular Surgery*, pp. 393–402.

"Endothelial Cell–seeded Artificial Prostheses for Coronary Bypass Grafting ", by T.J. Hunter, S.P. Schmidt, W.V. Sharp, R.F.Debski, M.M. Evancho, R.E. Clarke, and L.J. Falkow, *Trans Am Soc Artif Intern Organs*, vol. XXXII, pp. 339–341, 1986.

"In Vitro Cultivation and Immunogenicity of Human Cardiac Valve Endothelium", by A. Simon, MD, N. Zavazava, MD, PhD, H.H. Sievers, MD, PhD and W. Muller–Ruchholtz, MD, PhD., *J. Card Surg*, vol. 8, pp. 656–665, 1993.

"Human Xenoreactive Natural Antibodies–Avidity and Targets on Procine Endothelial Cells", *Transplantaion—Brief Communication*, vol. 56, pp. 1251–1292, Nov. 1993.

"Properties of Acellular Vascular Matrix", by R.C. Duhamel, K. Brendel, R.L. Reinert, J.M. Malone, Conference Paper; Conference entitled Biomaterials '84: Transaction—Second World Congress on Biomaterials, 10th Annual Meeting of the Society for Biomaterials, Sixteenth International Biomaterials Symposium—Washington, DC. Published by Soc for Biomaterials, San Antonio, TX, p.98, 1984.

"A Gelatin Membrane Substrate for the Transplantation of Tissue Cultured Cells", by M.M Jumblatt, B.D. Schwartz, *Transplantation (USA)*, pp. 498–499, 1980.

"Lifecell Corp: LifeCell begins Clinical Evaluation of its Processed Human Skin, AlloDerm", Byline: Business Editors, *The Woodlands, Texas (Business Wire)*, Aug. 17, 1992.

"Heterologous Heart Valves: Past, Present, and Future", by S.O. Burman, MD, *Ann Thorac Surg*, vol.48, 1989.

"Discordant Xenografting: A Summary and Look to the Future", by F.H. Bach, *Transplantation Proceedings*, vol. 24, No. 2 pp. 739–742, Apr. 1992.

Abbott, et al., "Absence of Antigenicity in Freeze–Dried Skin Allografts", *Cryobiology*, vol. 6, No. 5, 416–418 (1970).

Athreya, et al., "Differential Susceptibility of Epithelial Cells and Fibroblasts of Human Skin To Freeze Injury", *Cryobiology*, vol. 5, No. 4, 262–269 (1968).

Barlyn, et al., "Frozen Skin Autografts Protected by Dimethyl Sulfoxide", *Surgical Forum on Plastic Surgery*, vol. XV, 475–477 (Oct. 1964).

Berggren, et al., Clinical Use of Viable Frozen Human Skin:, *JAMA*, vol 194, No.2, 129–131 (Oct. 1965).

Bondoc, et al., "Clinical Experience with Viable Frozen Human Skin and a Frozen Skin Bank", Presented at Annual Meeting of American Surgical Association, Boca Raton, Florida (Mar. 24–26, 1971).

Brown, et al., "Laboratory Investigations of Skin Viability Following Preservation by Various Methods", *Surgical Forum on Plastic Surgery*, vol. VI 577–581 (Nov. 1955).

Chambler, et al., The Use of Etox Lyophilised Skin in Burns, *Journal Plastic Surgery*22(3) 210–215 (Jul. 1969).

Chalmers, "Transplantation Immunity in Bone Homografting", *Journal of Bone and Joint Surgery*, vol. 41B, No. 1, 160–179 (Feb. 1959).

Cinamon, et al., "A Simplified Testing System to Evaluate Performance After Transplantation of Human Skin Preserved in Glycerol or in Liquid Nitrogen", *Journal of Burn Care& Rehabilitation*, 435–439, (Jul./Aug. 1993).

Cochrane, et al., "The Low Temperature Storage of Skin: A Preliminiary Report", *Journal Plastic Surgery*, vol. 21 (1968).

Cram, et al., "Short–term Preservation of Human Autografts", presented at Annual Meeting of American Burn Association, New Orleans, LA (Mar. 1983).

De Loecker, et al.,"Metabolic Changes in Human Skin Preserved at −3 and at −196C", *Cryobiology* 17, 46–53 (1980).

De Loecker, et al., "Metabolic Changes in Rat Skin during Preservation and Storage in Glycerol Buffer at −196C", *Cryobiology* 12, 24–30 (1976).

Dogo, "Treatment of Extensively Burned Patients with Freeze–Dried Homologous Skin (a long term appraisal of the results)", *ACTA Chirgugiae Plasticae*, 187–198 (1965).

Friedlaender, et al., "Studies on the Antigenicity of Bone", *Journal Bone Joint Surgery (AM)*, 851–858 (Sep. 1976).

Georgiade et al., "A Clinical and Experimental Investigation of the Preservation of Skin", *Plastic & Reconstructive Surgery* vol. 17, No. 1, 267–275 (Apr. 1956).

Goldman, et al., "Lyophilized Veins as Arterial Interposition Allografts", *Cryobiology* 18, 306–312 (1981).

Graham, et al., "Versatility of Skin Allografts: Desirability of A Viable Frozen Tissue Bank", *The Journal of Trauma*, vol. 11, 494–501 (Jun. 1971).

Gresham, "Freeze–Drying of Human Tissue for Clinical Use", *Cryobiology*, vol. 1, No. 2, (1964).

Hayes, "Skin Homografts–A–Life–Saving Measure in Severely Burned Children", 22 Annual Session of American Association for Surgery of Trauma, Homestead, Hot Springs, VA (Oct. 1962).

Helenius, et al.,"Solubilization of Membranes by Detergents", *Biochimica et Biophysica Acta*, 415, 29–79 (1975).

Heiple, et al., "A Comparative Study of the Healing Process Following Different Types of Bone Transplantation ", *Journal of Bone and Joint Surgery*, vol. 45A No. 8, 1593–1616 (1963).

Hyatt, et al., "New Methods for Preserving Bone, Skin and Blood Vessels", *Postgraduate Medicine*, vol. 12, No. 3 (Sep. 1952).

Kearney, et al., "Cryopreservation of Skin Using a Murine Model: Validation of a Prognostic Viability Assay", *Cryobiology* 27, 24–30 (1990).

Konstantinow, et al., "Sking Banking: A Simple Method for Cryopreservation of Split–Thickness Skin and Cultured Human Epidermal Keratinocytes", *Annals of Plastic Surgery* vol. 26 No. 1 (Jan. 1991).

Lichtenberg, et al., "Solubilization of Phospholipids By Detergents", *Structural and Kinetic Aspects, Biochimica et Biophysica Acta* 737, 285–304 (1983).

Marrangoni, "An Experimental Study on Refrigerated Skin Grafts Stored in Ten Per Cent Homologous Serum", *Plastic& Reconstructive Surgery*, vol. 6 No. 6 (Dec. 1950).

McGregor, et al., "The Behaviour of Cialit–Stored and Freeze–Dried Human Fascia Lata in Rats", *Journal of Plastic Surgery* 155–164 (1974).

Nathan, et al., "Burn Wounds: Selection and Preservation of Skin, Natural Products, Blood, and Blood Products for Burn Therapy", *CRC Critical Reviews in Clinical Laboratory Sciences* 1–31 (May 1976).

Prows, et al., "Evaluation of Storage Conditions for Refrigerated Rabbit Skin", *Cryobiology* 17, 125–129 (1980).

Raju, et al., "Effect of Storage on Skin Allograft Survival", *Arch Surg*, vol. 99, 100–102 (Jul. 1969).

Reddi, Bone Matrix in the Solid State: Geometric Influence on Differentiation of Fibroblasts,*Adv Bio Med Phys* 1–18 (June 1974).

Swaim, "Skin Grafts", *Plastic and Reconstructive Surgery, Veterinary Clinics of North America: Small Animal Practice* vol. 20 No. 1, 147–175 (Jan. 1990).

Taylor, "Cryopreservation of Skin: Discussion and Comments", *Cryobiology* vol 3, No. 2, 192–196 (1966).

Wachtel, "Viability of Frozen Allografts", *American Journal of Surgery*, vol 138, 783–787 Dec. 1979).

Langdon, "Reconstitution of Structure and Cell Function in Human Skin Grafts Derived from Cryopreserved Allogeneic Dermis and Autologous Cultured Keratinocytes", *Journal Invest. Dermatology* vol. 91, 478–485 (1988).

May et al., "Recent Developments in Skin Banking and the Clinical Uses of Cryopreserved Skin", *Journal of MAG*, vol. 73, 233–236, (Apr. 1984).

Hoch et al., "In Vitro Endothelialization of an Aldehyde–Stabilized Native Vessel", *Journal of Surgical Research* 44, 545–554 (May 1988).

O'Brien, et al., A Comparison of Aortic Valve Replacement with Viable Cryopreserved and Fresh Allograft Valves, with a Note on Chromosomal Studies, J. Thoracic & Cardiovascular Surg. 94:812–823 (1987).

Slavkin, et al., Concepts of Epithelial–Mesenchymal Interactions During Development: Tooth and Lung Organogenesis, J. Cellular Bioch. 26:117–125 (1984).

Manu–Tawiah and Martin, Peat Extract as a Carbon Source for the Growth of *Pleurotus ostreatus* Mycelium, J. Sci. Food Agric. 47:243–247 (1989).

Nichols, et al., Cytogenetic Evaluation of Human Endothelial Cell Cultures, C. Cellular Phys. 132:453–462 (1987).

Nanchahal, et al., Cultured Composite Skin Grafts: Biological Skin Equivalents Permitting Massive Expansion, The Lancet 2 (1989) 22:191–193 (Jul. 22, 1989).

Shiogama, et al., An Improved Cryopreservation Procedure for Human Fetal Pancreas Tissues, Biological Abstracts, vol. 85, Abstract No. 46563 (1988).

Shingh, et al., Binding of Tumor–Derived Angiogenic Factor to High Affinity Receptor on Endothelial Cells, J. Cell Biology 103:299a, Abstract No. 1107 (1986).

Bell, et al., Living Tissue Formed in vitro and Accepted as Skin–Equivalent Tissue of Full Thickness, Science 211:1052–1054 (1981).

Weinberg and Bell, A Blood Vessel Model Constructed from Collagen and Cultured Vascular Cells, Science 231:397–400 (1986).

Kent, et al., Species Variation and the Success of Endothelial Seeding, J. Vascular Surg. 9:271–276 (1989).

Hoch, et al., In vitro Endotheliatization of an Aldehyde–Stabilized Native Vessel, J. Surg. Res. 44:545–554 (1988).

Noyes, Culture of Human Fetal Liver, Proc. Soc. Exp. Biol. Med. 144:245–248 (1973).

Leapman, et al., Transplantation of Fetal Intestine: Survival and Function in a Subcutaneous Location in Adult Animals, Ann. Surg. 179:109–114 (1974).

Brockbank, Repopulation of Xenograft Heart Valves with Fibroblasts, Small Business Innovation Research Grant Application No. PHS 90–2 (submitted Aug. 15, 1990).

TREATED TISSUE FOR IMPLANTATION AND METHODS OF TREATMENT AND USE

RELATED U.S. PATENT APPLICATIONS

The present application is a continuation of U.S. patent application Ser. No. 08/023,492, filed on Feb. 26, 1993 now U.S. Pat. No. 5,772,695 which is a continuation of U.S. patent application Ser. No. 07/664,902 filed on Mar. 5, 1991 now U.S. Pat. No. 5,192,312 entitled "Treated Tissue For Implantation and Methods of Treatment and Use".

During the last 20 years, allograft heart valve transplantation in the United States has increased from about 50 to 2,000 per annum. Because of the increase in demand, particularly in pediatric cases, utilization of allograft heart valves is now limited by the supply of donated human hearts.

The invention described herein relates to transplantable tissue, such as heart valves, which is treated to reduce potentially untoward reactions to the tissue which would otherwise result upon transplant. Implantable tissue has in the past been taken from patients and reimplanted into the same patient in a different site, such as with burn victims who require skin grafts and coronary bypass patients who require coronary arterial replacement using sections of saphenous veins.

Similarly, organs such as kidneys have been transplanted allogeneically from one sibling to another in an effort to minimize immunologically mediated reactions by the transplant recipient, which would result in organ rejection. These patients, as well as patients receiving transplant organs from donors other than siblings, are frequently administered drugs to suppress the immune system. While the immunological response to transplant tissue may be suppressed through the use of immunosuppressant drugs to minimize tissue rejection, immunosuppressant therapy is general in nature. Hence, immunosuppressant drugs also tend to suppress the immune response, which reduces the transplant patient's ability to combat infection.

The supply and ready availability of transplantable organs and graft tissue has been far outdistanced by the demand for such tissue over the past several years, and there is a long-felt need for an increase in the supply of such organs and tissue. This need remains to an extent unfilled, even taking into account the various synthetic tissues and mechanical organs which are presently available.

Bioprosthetic grafts are typically superior to mechanical prosthetic devices for various reasons. For example, mechanical heart valves are typically more prone to cause thromboembolism than bioprosthetic grafts. Moreover, mechanical equipment failures typically occur suddenly and without warning, resulting in emergency situations requiring surgical intervention and replacement of the artificial prosthetic device. Bioprosthetic heart valve grafts do not typically fail suddenly when a problem occurs. Rather, if there is a secondary valve failure, the valve tends to wear out gradually over time. This gives the patient and treating physician some advance warning that a graft prosthesis failure is likely to occur.

The invention described herein relates to xenogeneic or allogeneic tissues made suitable for transplant into a patient by replacing native cells within the tissue with autogenous or allogeneic cells. These modified grafts combine the advantages of bioprosthetic valves with immunological tolerance on the part of the recipient and the ability to maintain and repair the extracellular matrix.

There have been attempts at producing artificial tissues and organs in the past with varying degrees of success.

Steinberger, U.S. Pat. No. 4,407,787, relates to a dressing comprised of collagen and a resorbable biopolymer. The dressing is tissue-agglutinable, such that the dressing adheres to tissue and causes hemostasis.

Caplan, et al., U.S. Pat. No. 4,609,551, relates to a process for stimulating bone and cartilage growth, utilizing a soluble bone protein. The bone protein is combined with cells such as fibroblasts, and the mixture may be injected into the site of a joint cavity articular surface defect. Alternatively the bone protein and cells may be implanted in a fibrin clot. The fibroblasts differentiate to form replacement cartilage tissue.

Nevo, et al., U.S. Pat. No. 4,642,120, relates to a gel-type composition for repairing bone and cartilage defects. The gel contains mesenchymal cells which differenciate into cartilage cells through the influence of chondrogenic inducing factor in combination with fibrinogen, antiprotease and thrombin.

Bell, U.S. Pat. No. 4,485,096, relates to a tissue equivalent for treatment of burns or skin wounds and to fabricated prostheses. A hydrated collagen lattice is contracted with a contractile agent, e.g., fibroblasts or blood platelets, to create a collagen lattice which may then be populated with keratinocytes, thus forming a skin equivalent. Alternatively, glandular cells, such as pancreatic beta cells, or hepatocytes can be grown on the collagen lattice to produce a pancreas or liver tissue "equivalent". Bone equivalents can also be formed from the contracted collagen matrix described above in combination with demineralized bone powder.

Bell, U.S. Pat. No. 4,539,716, similarly relates to synthesized equivalents for blood vessels and glandular tissue. A contractile agent is used to contract the collagen lattice axially around an inner core. Additional layers containing capillary beds, blood vessels and glandular structures are then constructed.

Bell, U.S. Pat. No. 4,546,500, relates to the fabrication of blood vessels and glandular tissues utilizing a collagen lattice contracted axially around an inner core and combined with a plastic mesh sleeve. The plastic sleeve is sandwiched between layers of the matrix to reinforce the structure.

Bell, et al., U.S. Pat. No. 4,835,102, relates generally to tissue equivalent test systems, and includes tissue equivalents for epithelial, connective, cartilage, bone, blood, organs and glandular tissues as well as blood vessels. The tissue equivalent is composed of cultured cells which are derived from the endogenous tissue and incorporated into a collagen lattice.

Bell, et al., PCT Application WO 86/02273 published Apr. 24, 1986, relates to methods of forming living tissue equivalents, which utilize a collagen matrix contracted to form a lattice in a nutrient medium. The initially acidic collagen system is precipitated by raising the pH sufficiently to induce fibrillogenesis and the formation of a gel matrix containing cells.

Bell, et al., European Patent Application No. 89309972.1 relates to tissue equivalents which have cell types differentiated from progenitor cells without exogenous chemical induction. The tissue equivalent is in the form of a tissue precursor mixture which is non-gelled, and the mixture is injected into the host. The mixture gels and is space filling upon injection into the appropriate site. The cells must exhibit the ability to differentiate without exogenous chemical induction for the tissue equivalent to be effective.

Shing, Y. et al. *Cell Biology*, Vol. 103, No. 5, Pt. 2 Abstract No. 1107, page 299a (1986) relates to a chondrosarcoma derived growth factor which is angiogenic in vivo. The chondrosarcoma growth factor is used to stimulate endothelial cell proliferation in vitro.

Bell, et al. *Science* Vol.211, pp 1052–1054 (1981) relates to skin-equivalent grafts treated with a contractile agent to form a collagen lattice. The lattice is seeded with epidermal cells. The lattice allegedly permits vascularization of the graft.

Weinberg, C. B., et al., *Science* Vol. 231: 397–400 (1986), relates to a blood vessel model containing collagen and cultured vascular cells.

Kent, K. C. et al., *J. Vascular Surg.* Vol. 9, No. 2, pp 271 to 276 (1989), relates to endothelial seeding of vascular grafts in dogs, and the patency of the luminal monolayer. Endothelial cells harvested from bovine aorta, canine external jugular vein and human saphenous vein are compared.

Hoch, J. et al. *J. Surg. Res.* vol. 44, No. 5, pp. 545 to 554, relates to the use of Dacron and polytetrafluoroethylene polymeric grafts, as well as bovine carotid artery heterografts which were compared in vitro to determine the extent of endothelial cell adherence.

Noyes, W. F. *Proc. Soc. Exp. Biol. Med.* Vol. 144, No. 1 pp. 245–248 (1973) relates to human liver cell cultures which utilize collagen as a substrate. Gel-foam sponge is also used as a substrate.

The present invention relates to a transplantable or implantable xenogeneic or allogeneic tissue having immunogenic sites which if untreated, would ordinarily induce an immune system response in the patient, ultimately leading to transplant rejection. Similarly, a method is described of rendering the transplantable tissue substantially non-immunogenic by replacing native cells with allogeneic or autologous cells, reducing the recognition of a transplanted graft as a foreign substance without generally suppressing the patient's immune system.

In particular, the present invention relates to transplantable tissue which can be treated in accordance with the methods described herein to reduce or prevent untoward immune system reactions which the recipient may experience in response to the graft, which in turn minimizes transplant rejection. Hence, one object of the present invention is to reduce patient rejection of transplanted tissue.

A further object of the present invention is to increase the supply of transplantable tissue by treating grafts to render them suitable for transplant into human patients in need of such treatment.

A further object of the present invention is to facilitate the use of animal donors that can supply xenograft donor tissue in virtually unlimited quantities. The donor tissue can be transplanted into human recipients after the tissue has been treated in accordance with the methods described herein.

Additional objects of the present invention will be apparent to those skilled in the art from the teachings herein.

SUMMARY OF THE INVENTION

The invention described herein includes a transplantable bioprosthetic graft tissue which is treated prior to transplant with a growth factor and then exposed to cells which are attracted into the tissue and proliferate in response to the growth factor and populate the transplantable tissue. Replacement of cells effectively reduces immune responses to the tissue, thus improving the effective life of the graft and reducing the frequency, incidence and severity of transplant rejection.

The invention further addresses a method of treating xenogeneic transplantable tissue which comprises exposing the tissue to a growth factor and then culturing the graft tissue with cells which migrate and proliferate in response to the growth factor, thus populating the tissue with the cells to enhance the effective life of the tissue upon transplant, and reduce any immunologically mediated adverse effects which the graft recipient otherwise experiences in response to the xenogeneic tissue upon transplantion.

DETAILED DESCRIPTION

Figure 1:
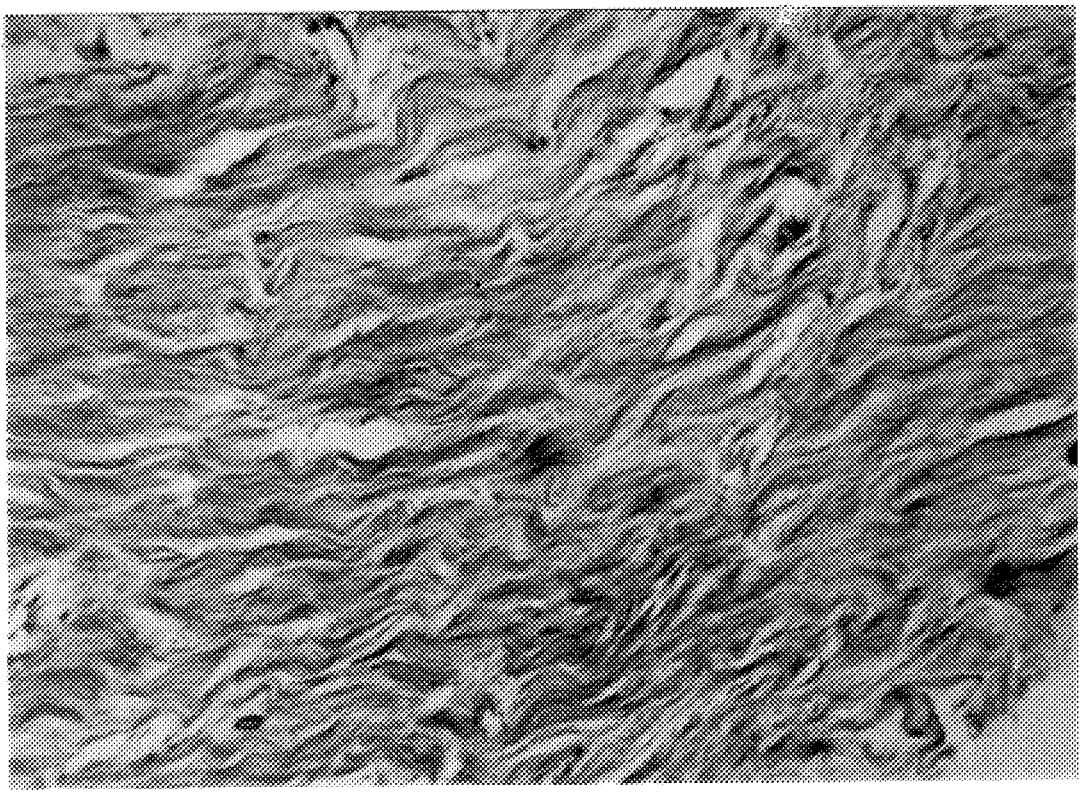
FIG. 1 is a photomicrograph of control tissue not exposed to growth factor.

The terms "tissue", "organ" and "organ part" are used in the general sense herein to mean any transplantable or implantable tissue, organ or organ part, the survivability of which is improved by the methods described herein upon implantation. In particular, the overall durability and longevity of the implant are improved, and host-immune system mediated responses, e.g., graft rejection, are reduced in severity as well as in frequency, and may be eliminated altogether.

The terms "transplant" and "implant" are used interchangably to refer to tissue or cells (xenogeneic or allogeneic) which may be introduced into the body of a patient to replace or supplement the structure or function of the endogenous tissue.

The term "autologous" refers to tissue or cells which originate with or are derived from the recipient, whereas the terms "allogeneic" and "allograft" refer to cells and tissue which originate with or are derived from a donor of the same species as the recipient. The terms "xenogeneic" and "xenograft" refer to cells or tissue which originates with or is derived from a specie other than that of the recipient.

The invention described herein is particularly useful for bioprosthetic xenografts in which the major structural component is connective tissue matrix. Examples of such grafts include bioprosthetic heart valves, blood vessels, ligaments and tendons.

Hence, a preferred aspect of the invention encompasses a xenograft treated with a growth factor and incubated with cells that migrate and proliferate in response to the growth factor, thus populating the xenograft, said replacement of cells being effective for reducing allergic complications upon transplant when compared to untreated xenografts.

Upon treatment of the xenograft with growth factor according to the methods described herein, and upon population of the xenograft with allogeneic or autogenous cells that improve the viability of the xenograft after transplant and reduce any immune response to the xenograft, there is a reduced tendency for thromboemboli to occur, particularly when compared to mechanical heart valves. This results in increased implant longevity, decreased or slowed degeneration of the implant, and decreased adverse immune reactions which otherwise may result in host rejection.

The preferred growth factor for use herein is fibroblast growth factor, in particular, basic fibroblast growth factor ("bFGF"). When used to treat xenograft implants, such as heart valves, the graft may be initially exposed to a buffered nutrient medium, and then immersed in a solution containing bFGF. Optionally the graft may be sterilized and rendered acellular using an effective dose of radiation or a cytotoxic solution prior to treatment with bFGF.

The concentration of growth factor used to treat the xenograft typically ranges from about 100 ng/ml to 10 mg/ml with a growth factor concentration for bFGF of about 2.5 mcg/ml being most preferred.

The graft is bathed in the solution containing growth factor for a time period which is effective for causing cells which migrate and proliferate in response to the growth factor to adhere to and penetrate the surface of the xenograft. This, in effect, causes the cells to populate the xenograft.

To populate (or repopulate) the graft with cells, the graft may be washed, immersed in a growth factor containing solution, and then placed into a suitable buffered medium containing the cells which migrate and proliferate in response to the growth factor, thus populating the graft tissue with cells. The graft and cells are cultured together at a temperature and for a time period which are effective for causing the cells to populate and adhere to the graft.

Culture times range from about 3 to 21 days. Culture times may be reduced somewhat by increasing the initial concentration of cells.

When fibroblasts are used as the graft-populating cells, the graft may typically be immersed in Dulbecco's Modified Eagle medium with 5% serum. The graft is cultured with a primary fibroblast culture for about three days. Additionally the graft may be secured on the culture plate and incubated at about 37° C. in a humidified atmosphere, until the graft has been populated with fibroblasts, e.g. 5% $CO_2$/95% air. Incubation is considered complete when the fibroblasts have populated the graft in such a manner that the graft appears histologically similar to a fresh graft. (e.g., a normal cell distribution).

Essentially any buffered physiological salt solution containing protein carriers can be employed.

Preferred buffers for use with the growth factor include sodium phosphate/glycerin/bovine serum albumin ("BSA"). These buffers typically are used to provide a physiologically acceptable pH, such as about 7.0 to 7.6.

The cells which are used to populate the graft can be varied within wide limits, and different types of cells can be used in different circumstances, depending upon the site and size of the transplant, the nature of the tissue to be replaced, the allergic sensitivity (or hypersensitivity) of the patient and other factors.

The graft may be sterilized prior to treatment with the growth factor, or treated to kill off the endogenous cells in the graft prior to treatment with growth factor and subsequent graft population. This may reduce the likelihood of microorganismal contamination as well as the immunogenicity of the graft prior to graft population and implantation. A preferred method for sterilizing grafts prior to population utilizes radiation exposure, e.g., x-rays in lethally effective doses. Alternatively, antibiotics, antibacterials and cytotoxic agents in normally effective doses may be used.

A preferred aspect of the invention involves the use of autogenous cells in the process described herein. In this instance, a tissue sample is taken from the patient prior to transplant surgery. The tissue is treated in accordance with the methods described herein to produce fibroblasts or other cells which are then used to repopulate the graft. By immersing the graft in growth factor and a culture of autogenous cells, and by populating the graft with cells derived from the resected tissue taken from the patient, an adverse immune system response and ultimately graft rejection can be minimized or avoided.

The cell source tissue can be selected to match the tissue to be transplanted. For example, if a blood vessel is to be transplanted, cells can be taken from a patient, healthy blood vessel and used as the source of cells for graft population. In this fashion, the healthy graft can be very closely matched to the patient's diseased tissue.

This aspect of the invention is particularly useful when the transplant patient is highly allergic, or if the tissue is highly immunogenic, such as with respect to transplantable blood vessels.

Alternatively, cell lines can be used to repopulate the graft which are substantially non-immunogenic. Cells which elicit no more than a weak allergic response are used to populate the graft prior to transplant.

Method for Isolation of Fibroblasts

The tissue, for example skin or heart valve leaflet, is cut into 1 $mm^3$ pieces using a sterile dissection technique. Groups of 10 pieces are then placed in 35 $cm^2$ tissue culture dishes with approximately 1 ml of culture medium (DMEM+10% FCS). It is important that the pieces of tissue remain attached to the plastic surface of the culture dish; if the tissue detaches, the amount of culture medium should be reduced. Incubate for 1 week at 37° C. in a humidified culture incubator. After 1 week of incubation, each piece of tissue is surrounded by a dense outgrowth of fibroblasts. Epithelial cells may also be present but are lost during subsequent cell culturing. The fibroblasts are removed with a plastic scraper or by collagenase digestion after rinsing the cells with a calcium and magnesium-free buffered salt solution, and placed in larger cell culture vessels with fresh culture medium. The cell cultures can be expanded in this manner. The contents of one flask can be divided and placed into three larger vessels, and this process can be repeated about once a week for at least 10 weeks. These flasks of fibroblasts are then utilized as a cell source. Cells obtained in this manner are preferable to commercially available cell lines, because most cell lines are genetically modified and are no longer responsive in a normal manner to growth regulators (such as FGF).

The fibroblasts can be either immunologically matched allogeneic cells, such that the recipient does not recognize them as foreign, or autologous cells, in which case the donor and recipient are the same individual.

Results

A study was performed using canine leaflets and bovine fibroblasts. Mitral valve leaflets were aseptically harvested from a dog cadaver shortly after it was killed. The leaflets were divided into sections and placed in petri dishes containing 5 ml $NaH_2PO_4$/glycerin/BSA buffer. The leaflets were irradiated with 4,000 cGy of 6 MV x-rays to kill the donor cells. The leaflets were then placed in HBSS (Hanks Balance Salt Solution) with 0.25% trypsin for 10 minutes to remove any residual endothelial cells. The trypsin was inactivated by adding cold culture medium with 5% serum. The leaflets were washed and placed in $NaH_2PO_4$/glycerin/BSA buffer. Human recombinant bFGF was added to the $NaH_2PO_4$/glycerin/BSA buffer in the following concentrations: 0, 50, 500, and 2,500 ng/ml and incubated for 4.5 hours.

The stock solution of bFGF was prepared with sodium heparin added in a 3:1 bFGF:heparin (w/w) ratio. Aliquots and the bFGF stock solution were stored at −70° C.

After incubation, the leaflets were washed in phosphate buffered saline and placed in DMEM (with non-essential amino acids and penicillin/streptomycin) with 0.5% fetal calf serum ("FCS"). Bovine fibroblasts, which had previously been obtained from calf aorta by standard explant techniques were added to the heart valve leaflets at $2\times10^4$ cells/ml. The heart valve leaflets were then secured to the bottom of the plate with small weights and incubated for 10 days at 37° C. in a humidified 5% $CO_2$ and 95% air environment.

Figure 2:
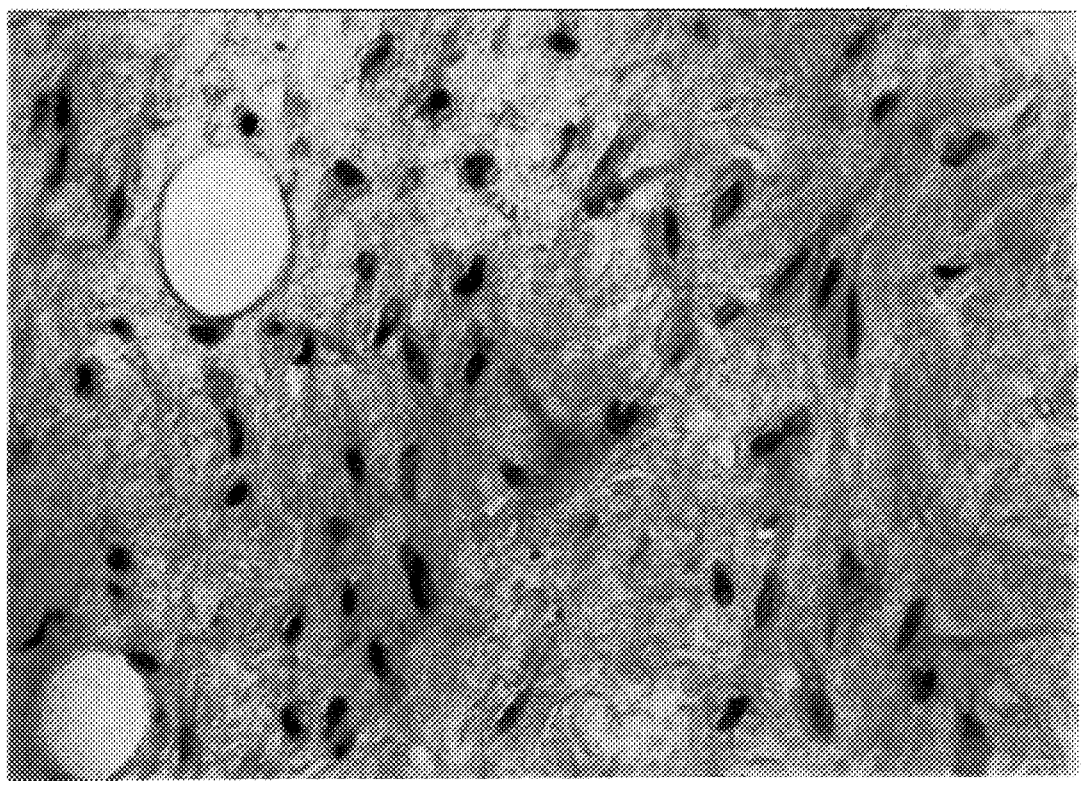
FIG. 2 is a photomicrograph of tissue exposed to basic fibroblast growth factor ("bFGF") (2500 ng/ml) and incubated with fibroblasts for 10 days.

Following incubation, valve sections were placed in formalin for histopathological analysis. The analysis demonstrated that there was a bFGF dose-dependent increase in fibroblast ingrowth into the heart valve leaflets. For example representative micrographs in FIG. 1 show the control leaflets not exposed to bFGF were essentially acellular, whereas leaflets exposed to 2500 ng/ml bFGF shown in FIG. 2 were well populated with cells. These results demonstrate that fibroblasts will populate an irradiated FGF-treated xenograft.

The description contained herein contains the preferred embodiments of the invention. However, numerous alternative embodiments are contemplated as falling within the scope of the invention.

I claim:

1. A method of reducing the immunogenicity and improving the longevity of an implantable natural tissue comprising:

harvesting a bodily tissue suitable for transplantation into a patient, treating the bodily tissue prior to implantation with a growth factor, and populating the tissue throughout with cells that respond to the growth factor prior to implantation such that the bodily tissue retains the natural morphology of untreated tissue, wherein the cells are effective for reducing the patient's immune response to the tissue upon implant.

2. A method of reducing transplant tissue rejection comprising:

harvesting a bodily tissue suitable for transplantation into a patient, treating the bodily tissue prior to implantation with a growth factor, and populating the treated tissue with cells that respond to the growth factor prior to implantation such that the bodily tissue retains the natural morphology of untreated tissue, wherein the cells are effective to reduce tissue rejection upon transplant.

3. The method of claim 1 wherein the tissue is sterilized prior to the treatment with growth factor.

4. The method of claim 2 wherein the tissue is sterilized prior to treatment with the growth factor.

5. The method of claim 4 wherein the tissue is exposed to radiation prior to treatment with the growth factor.

6. The method of claim 3 wherein the tissue is exposed to radiation prior to treatment with the growth factor.

7. A method according to claim 1 wherein the cells comprise fibroblast cells.

8. A method according to claim 1 wherein the growth factor is effective on fibroblast cells.

9. A method according to claim 8 wherein the growth factor effective on fibroblast cells is basic fibroblast growth factor.

10. A method according to claim 8 wherein the growth factor effective on fibroblast cells is acidic fibroblast growth factor.

11. A method according to claim 2 wherein the cells comprise fibroblast cells.

12. A method according to claim 2 wherein the growth factor is effective on fibroblast cells.

13. A method according to claim 12 wherein the growth factor effective on fibroblast cells is basic fibroblast growth factor.

14. A method according to claim 12 wherein the growth factor effective on fibroblast cells is acidic fibroblast growth factor.

15. A method of reducing immunogenicity and improving the longevity of an implantable natural tissue, comprising a) harvesting a bodily tissue suitable for transplantation into a patient, b) treating the bodily tissue to eliminate endogenous cells from the tissue; and c) repopulating the bodily tissue with cells in the presence of growth factor to promote cell-repopulation of the implantable tissue, wherein the bodily tissue retains the natural morphology of untreated tissue and the cells respond to the growth factor and are effective to reduce tissue rejection upon transplant.

16. The method of claim 15 wherein the tissue is selected from the group consisting of connective tissue, heart valves, blood vessels, ligaments and tendons.

* * * * *